United States Patent [19]

Lai

[11] Patent Number: 5,034,523
[45] Date of Patent: Jul. 23, 1991

[54] PROCESS FOR PREPARING A 1,4-DIAZACYCLOHEPTAN-2-ONE WITH A MIXTURE OF ALKYLATED DIAMINES

[75] Inventor: John T. Lai, Broadview Heights, Ohio

[73] Assignee: The BF Goodrich Company, Akron, Ohio

[21] Appl. No.: 462,153

[22] Filed: Jan. 8, 1990

[51] Int. Cl.$^5$ ........................................... C07D 243/08
[52] U.S. Cl. .................................................... 540/492
[58] Field of Search ........................................ 540/492

[56] References Cited

U.S. PATENT DOCUMENTS

| | | |
|---|---|---|
| 4,167,512 | 9/1979 | Lai ........................................ 540/492 |
| 4,246,412 | 1/1981 | Lai ........................................ 540/492 |
| 4,297,497 | 10/1981 | Lai ........................................ 540/492 |
| 4,466,915 | 8/1984 | Lai ........................................ 540/492 |

Primary Examiner—Robert T. Bond
Attorney, Agent, or Firm—Alfred D. Lobo

[57] ABSTRACT

A process is disclosed for making a 1,4-diazacyclo-heptan-2-one from a mixture ('first' mixture) of alkylated 1,3-propanediamines one of which (referred to as the 'target' diamine) has substituents at specified positions and contains (i) a terminal primary amine group adjacent to a disubstituted C atom (hence, referred to as having a 'hindered' N atom), and (ii) a terminal secondary amine group. The target diamine, other diamines and oligomeric polyamines in the first mixture, are made by alkylating an acyclic ('starting') 1,3-propanediprimaryamine having the hindered N atom. The first mixture of alkylated diamines, preferably containing a major molar proportion of the target diamine relative to any other alkylated diamines, is reductively alkylated, which unexpectedly results in the reductive alkylation of only the unwanted diamines, allowing the target diamine which is not reductively alkylated, to be removed from the mixture of reductively alkylated diamines. Upon cyclization of the target diamine, using the "ketoform reaction", it is essentially quantitatively converted to the 1,4-diazacycloheptan-2-one having an unsubstituted $N^4$ atom flanked by disubstituted adjacent C atoms. By removing the unwanted components in the reaction mass an essentially pure product of 1,4-diazacyclopheptan-2-ones is recovered. Thus, the difficulty of separating the target amine from other close-boiling compounds is avoided. As an alternative, the reductive alkylation step can be bypassed and the first mixture subjected to the ketoform reaction, followed by recovery of the desired product.

34 Claims, No Drawings

PROCESS FOR PREPARING A 1,4-DIAZACYCLOHEPTAN-2-ONE WITH A MIXTURE OF ALKYLATED DIAMINES

BACKGROUND OF THE INVENTION

Over the past many decades, commercial interest in alkylated diamines has been frustrated by the difficulty of separating a desired or 'target' diamine in a mixture (first) of alkylated diamines all of which have molecular weights in so narrow a range as to make separation of individual diamines in such a first mixture impractical. Frustration in making a desired separation is evidenced by the high cost of obtaining suitably pure precursors for the preparation of a wide spectrum of amine-based compounds, for example, piperidine, piperazine, and piperazinone-based hindered amine light stabilizers.

Only the target diamine or bis-compound thereof (referred to herein as a "bis-target diamine") is desired for the preparation of a polysubstituted 1,4-diazacycloheptan-2-one disclosed in Lai U.S. Pat. Nos. 4,167,512; 4,297,497 and 4,466,915, the disclosures of which, particularly those relating to the ketoform reaction, are incorporated by reference thereto as if fully set forth herein. In a manner analogous to that illustrated in Exs 1-3 of the '915 patent, it is most desirable to start with the target diamine or bis-target diamine in essentially pure form. By "essentially pure" diamine we refer to a purity of at least 90% by weight. For example, the target diamine $N^1$-butyl-4-methyl-2,4-pentanediamine, is reacted with a ketone and chloroform in the presence of an alkali metal hydroxide, with or without a phase transfer catalyst, to form $N^1$-(butyl)-3,3,5,5,7-pentamethyl-1,4-diazepin-2-one having a seven-membered ring. In such a ring, each of the $N^4$-adjacent 3- and 5-carbon atoms is disubstituted so that the $N^4$ atom is said to be "fully" hindered. However, making the appropriately substituted target diamine or bis-target diamine in essentially pure form is an impractical and difficult task.

The $N^4$ atom in the 1,4-diazacycloheptan-2-ones is referred to as being "fully hindered" when it is flanked by adjacent disubstituted C atoms: the $N^4$ atom is referred to as being "partially" hindered when it is flanked by one adjacent disubstituted C atom and one monosubstituted C atom.

The task is impractical because, despite the alkylation of a 1-disubstituted-1,3-propanediamine (referred to as the "starting" diamine) being relatively straightforward, the reaction between alkyl halides and diprimary amines does not produce only the "expected" alkylated diamine. The reaction does not stop after alkylation of the less hindered primary amine group in the starting diamine, but also alkylates the hindered primary amine group. Thereafter the secondary amine groups of the alkylated starting diamine are further alkylated forming oligomers of the starting diamine. By "expected" diamine we refer to one which would be expected to form in a textbook application of an alkylation reaction.

One particular target diamine of interest herein is mainly used as a precursor for 1,4-diazacycloheptan-2-one-based light stabilizers disclosed in references hereinabove. The target diamine is represented by the structure

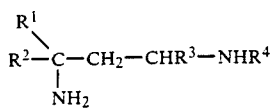

wherein, $R^1$, $R^2$, and $R^3$ independently represent $C_1$–$C_{24}$ alkyl (having from 1 to 24 carbon atoms);

$R^3$, but only one of $R^1$ and $R^2$, represent $C_7$–$C_{20}$ aralkyl;

$R^4$ represents $C_1$–$C_{20}$ alkyl, $C_5$–$C_{24}$ cycloalkyl or alkyl-substituted cycloalkyl, the ring being $C_5$–$C_8$; $C_7$–$C_{20}$ aralkyl, and $R^1R^2C$=$CR^1$-$CH_2$—; and, $R^1$ and $R^2$ together when cyclized represent $C_5$–$C_7$ cycloalkyl.

Also of particular interest is a bis-target diamine used as a precursor for a bis-1,4-diazacycloheptan-2-one light stabilizer in which polysubstituted 1,4-diazacycloheptan-2-one moieties are connected by a divalent radical. The bis-target diamine is represented by the structure

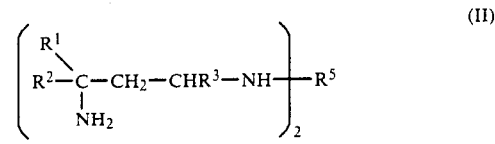

wherein, $R^5$ represents $C_2$–$C_{24}$ alkylene, $R^5$-substituted $C_9$–$C_{23}$ cycloalkyl the cycloalkyl ring being $C_5$–$C_8$; and, $R^8$—Ph—$R^8$ wherein Ph represents phenyl and $R^8$ represents $C_2$–$C_{12}$ alkylene.

In one embodiment, this process capitalizes on the ability to reductively alkylate only those diamines which one wishes to exclude from the feed to a subsequent ketoform reaction, so that the target diamine may be conveniently separated from the reductively alkylated mixture.

In another embodiment, this process side-steps the problem of separating the individual components of the alkylated first mixture by using the entire mixture of alkylated diamines in a ketoform reaction which results in conversion of essentially all the target diamine to desired 1,4-diazacycloheptan-2-one product. The 1,4-diazacycloheptan-2-one product is unexpectedly easy to isolate from a reaction mass which is a mixture (second) containing unreacted ketone and diamine reactants, alkali metal hydroxide, phase transfer catalyst, alkali metal salt and the 1,4-diazacycloheptan-2-one product among other unwanted cyclic and acyclic diamines.

Diprimary amines of particular interest having a hindered N atom, are represented by the structure

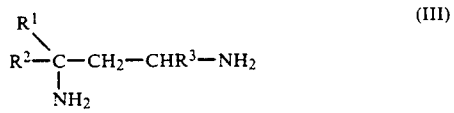

These are commercially available 1-disubstituted-1,3-propanediamines used as starting materials for a conventional alkylation reaction which produces the first mixture of alkylated diamines.

With particular respect to the diamine (I), though the disubstituted $N^2$-adjacent C atom provides a measure of steric hindrance to the $N^2$-amino group, it is nevertheless alkylated to a surprisingly large extent, in preference to the $N^1$-amino group even when only one mol of alkylating agent is used for two mols of starting diamine. If only one or the other of the primary amino groups of the starting diamine is alkylated with a monohalide, the alkylated diamine contains one secondary amino group. In addition, both primary amino groups are found to be alkylated, resulting in some of the alkylated product having terminal secondary amino groups. This clearly indicates that even when the starting diamine and alkylating agent are present in a molar ratio of 2:1 the $N^1$ and $N^2$ atoms are both alkylated to a surprisingly large extent.

If the halide is a dihalide, not only bis-compounds are formed having both primary and secondary groups, or, only secondary amino groups, but each of these may be further alkylated (as shown herebelow) producing still more unwanted byproduct diamines including oligomers having from 3 to about 6 diamine repeating units.

Therefore when both amine groups are primary, or when both primary and secondary amine groups are present in the amine to be alkylated, a wide assortment of alkylated products is formed even under the most controlled conditions (see "Advanced Organic Chemistry Reactions, Mechanisms and Structures" by J. March, 3d edition, btm of pg. 365 John Wiley & Sons 1984.) For this reason, generally, alkylation with an alkyl halide is used where a tertiary amine is desired and one expects to effect complete alkylation of all amine groups. Even carefully controlled conditions generally give a mixture of alkylated products and is not favored even on a laboratory scale.

To be sure, one might expect a much larger amount of the $N^1$-amino group to be alkylated in preference to the $N^2$-amino group, if one used substantially less than a molar equivalent of the alkylating agent, with the expectation that essentially all the unhindered $N^1$-amino group will be alkylated first. It is not. For example, only 0.5 mol of monohalide $R^4X$ or $XR^5X$ (defined herebelow) per mole of starting diamine will result in so large an assortment of alkylated products as to make using the first mixture impractical. Yet, by using a larger molar excess of starting diamine than 3:1, the process of this invention effectively produces a major molar proportion of the alkylated diamine in which the $N^2$-amino group is not alkylated. The alkylated diamines in the first mixture then yield an essentially pure product of 1,4-diazacycloheptan-2-ones which are recovered from a reaction mixture ("second" mixture) resulting from subjecting the first mixture to a ketoform reaction, explained in detail in the aforesaid Lai patents.

By an "essentially pure" product we refer to one in which the polysubstituted 1,4-diazacycloheptan-2-ones containing either a fully or partially hindered $N^4$ atom, constitute at least 90% by weight. In the product, the 1,4-diazacycloheptan-2-one with the fully hindered $N^4$ atom is preferentially formed, that is, it is present in a major molar amount relative to the amount of that with a partially hindered $N^4$ atom due to an idiosyncracy of the ketoform reaction. This idiosyncracy is at least in part attributable to the combination of the $N^2$-adjacent disubstituted C atom and the required presence of a substituent on the $N^1$-adjacent C atom.

In some instances, despite using more than a threefold, and preferably more than a four-fold excess, the first mixture still contains too many alkylated byproducts to provide a practical feedstream for the ketoform reaction. It is therefore necessary to concentrate the target diamine and remove it from the first mixture. It was found that, if the first mixture is reductively alkylated with a relatively high molecular weight halide, the reductively alkylated products are so physically different from the target diamine that the latter is easily separable. This is because, quite unexpectedly, the target diamine is not reductively alkylated, thus making it easy to distill, or otherwise separate it from the resulting mixture.

The reductive alkylation of acyclic diamines is well known and described with numerous examples, in the chapter entitled "Preparation of Amines by Reductive Alkylation" by W. S. Emerson in *Organic Reactions,* Vol 4, John Wiley & Sons, New York, N.Y. Examples are given for preparation (A) of tertiary amines from (i) secondary aliphatic amines and ketones, (ii) aryl alkyl amines and aliphatic aldehydes, (iii) aryl alkyl amines and ketones; etc., and, (B) of secondary amines by (i) reduction of Schiff's bases derived from aliphatic amines, and from aromatic amines, and (ii) reduction of primary aromatic amines, nitro or nitroso compounds and ketones, etc. In reductive alkylations with an aldehyde there is a wide scatter of side reaction because of the higher reactivity of an aldehyde than a ketone. There is no teaching that reductive alkylation of a substituted 1,3-propanediamine with a ketone will result in alkylation only at secondary amino groups, and at a primary amino group having a monosubstituted adjacent C atom. With particular respect to a reductive alkylation of diamines, triamines, tetramines, or polyamines generally, nowhere is there any suggestion that such a reaction may be used as a 'dynamic sieve' which allows only the desired target diamine to be recovered unaffected.

SUMMARY OF THE INVENTION

It has been discovered that when a 1-disubstituted-1,3-propanediprimaryamine is alkylated with less than one-third, and preferably from one-fourth to one-twentieth the theoretical amount of an alkylating agent that is required to alkylate a single primary amine group of the starting diamine, the mixture of plural alkylated 1,3-propanediamines contains a major molar amount of the target diamine (I); then, without separating the target diamine (I), the entire mixture of alkylated diamines can be subjected to a "ketoform reaction" to cyclize only those alkylated diamines which contain a primary amine group. The reaction mass, after cyclization, results in a large number of unwanted byproducts along with fully and partially hindered 1,4-diazacycloheptan-2-ones which have the structures (IV) and (V) respectively:

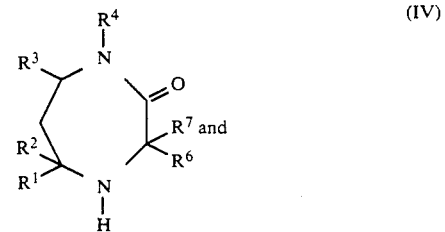

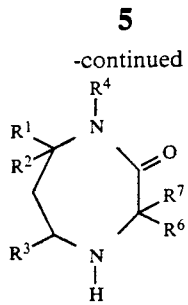

(V)

wherein, $R^6$ and $R^7$ are derived from the ketone reactant used, independently representing $C_1$-$C_{18}$ alkyl; and when together cyclized represent $C_5$-$C_8$ cycloalkyl.

The ketoform reaction typically produces from about 60% to 90% by weight of the fully hindered polysubstituted 1,4-diazacycloheptan-2-one, relative to the combined weight of polysubstituted 1,4-diazacycloheptan-2-ones in the product. Thus, the desired product is formed from a 1-disubstituted-1,3-propanediamine ('starting' diamine) having a hindered $N^2$ atom without making a separation one would otherwise expect to make if using a prior art process.

It is therefore a general object of this invention to provide a process for producing and separating 1,4-diazacycloheptan-2-ones from a mixture of alkylated 1-disubstituted-1,3-propanediamines only one of which (referred to as the 'target' diamine) contains a primary amine group with an adjacent disubstituted C atom (hence "hindered $N^2$ atom"); and, to produce the fully hindered 1,4-diazacycloheptan-2-one in a major molar proportion relative to any partially hindered one.

It is a specific object to provide a process comprising,
(a) alkylating the 'starting' diamine with less than 0.33 times, and preferably less than about 0.25 to 0.05 times the stoichiometric amount of alkylating agent required to alkylate only one primary amine group, so as to produce a reaction mass in which there is a major molar amount of the target diamine relative to other alkylated diamines and oligomeric polyamines;
(b) removing excess starting diamine from said reaction mass leaving a first mixture of alkylated diamines;
(c) subjecting the first mixture to a "ketoform reaction", and essentially quantitatively converting the target diamine in the mixture to a polysubstituted 1,4-diazacycloheptan-2-one having a fully hindered $N^4$ atom, present in a major molar proportion relative to one having a partially hindered $N^4$ atom; and,
(d) recovering the polysubstituted 1,4-diazacycloheptan-2-ones in essentially pure form.

The 1,4-diazacycloheptan-2-ones are recovered in essentially pure form by removing the solvent used in the reaction, and the alkali metal salt formed, then concentrating the reaction mass to yield the essentially pure 1,4-diazacycloheptan-2-ones. Thus the difficulty of separating the target amine from other close-boiling compounds is avoided.

It has also been discovered that, in those instances where it is desired to isolate the target diamine before cyclizing it, the target diamine may be isolated by reductively alkylating the first mixture; then separating essentially pure target diamine from the reductively alkylated mixture.

It is therefore a specific object of this invention to provide an additional processing step which allows facile separation of the target diamine when such separation is desired. When the first mixture of alkylated diamines (produced by alkylation) is reductively alkylated, the target diamine is not reductively alkylated, so that it can be separated from the mixture of reductively alkylated diamines, for example, by distillation. The target diamine so obtained is then subjected to the ketoform reaction.

When the alkylating agent is a dihalide $XR^5X$, bis-compounds and oligomers containing from 3 to about 6 diamine repeating units are formed. When the bis-compounds are subjected to a base-induced, preferably phase transfer catalyzed, ketoform reaction, bis-compounds are formed having the structures:

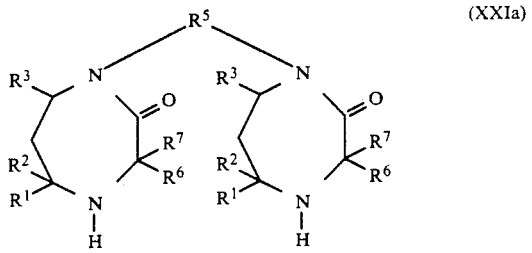

(XXIa)

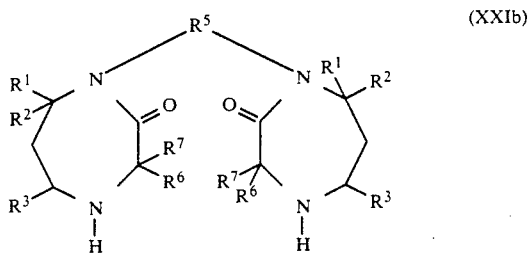

(XXIb)

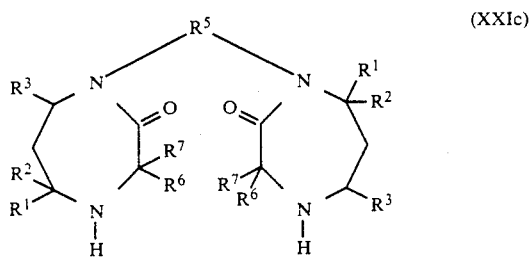

(XXIc)

DETAILED DESCRIPTION OF PREFERRED EMBODIMENTS

As will be evident from the foregoing, the problem is to form a particular 1,4-diazacycloheptan-2-one (IV) in a major molar proportion relative to (V) because the "fully" hindered $N^4$ atom provides more effective stabilization than the "partially" hindered one. Because (IV) and (V) each have a total of at least three substituents on the $N^4$-adjacent C atoms, (IV) and (V) are referred to as being "polysubstituted" 1,4-diazacycloheptan-2-ones.

The first step of the process comprises alkylating a starting diamine having the structure (II) present in at least a three-fold molar excess, with an aliphatic, alicyclic or heterocyclic halide $R^4X$ or dihalide $R^5X_2$ which alkylation reaction results in the first mixture (of alkylated 1-disubstituted-1,3-propanediamines). Typically, a five-fold molar excess, and as much as a ten-fold molar excess, of starting diamine is used. The amount of excess used will vary with different halides. Because excess starting diamine is to be removed, typically by distillation, to leave the first mixture, only as much excess as is needed to minimize the formation of unwanted alkylated diamines, is used.

When a halide R⁴X, preferably a chloride or bromide, is used, the reaction mass contains the target diamine (I) and at least the following diamines:

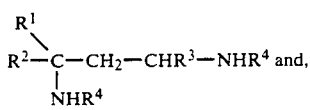

(VI)

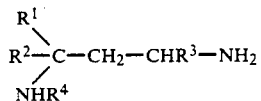

(VII)

In the second step, the excess starting diamine is separated from the alkylated reaction mass, typically by distillation, thus leaving the first mixture of alkylated diamines.

After separating excess starting diamine, but without separating any alkylated component of the first mixture of alkylated diamines, it (the first mixture) is subjected to a ketoform reaction during which (I) and (VII) cyclize to form the 1,4-diazacycloheptan-2-ones (IV) and (V), but (VI) does not cyclize. The target diamine (I) is present in a major molar amount relative to any other diamine, and (I) is the preferred diamine precursor because it results, upon cyclization, in a "fully" hindered 1,4-diazacycloheptan-2-one.

When a dihalide XR⁵X is used, the alkylated reaction mass contains not only (II) but also at least the following bis-compounds, in addition to halides and oligomers (not shown):

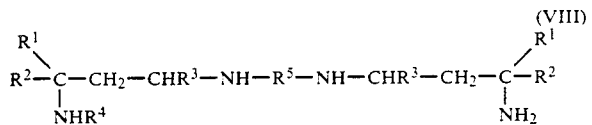

(VIII)

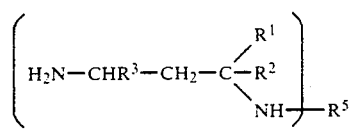

(IX)

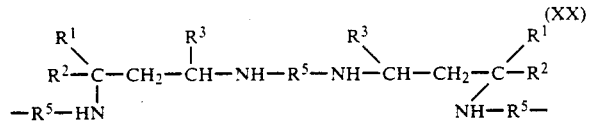

(XX)

the oligomers having from 3 to about 6 diamine repeating units.

After separating excess starting diamine, but without separating any alkylated component of the reaction mass obtained in the foregoing alkylation, the first mixture of alkylated diamines is subjected to a ketoform reaction during which (II) and (VIII) cyclize to form the bis-(1,4-diazacycloheptan-2-ones), but (IX) does not form the bis-compound.

In some instances it is desirable to make a separation of the first mixture to concentrate if not isolate the target diamine. In such instances, the first mixture is reductively alkylated with a ketone in the presence of a Group VIII metal hydrogenation catalyst and an inert solvent for the reactants under hydrogenation conditions, by carrying out the reaction under elevated pressure in the range from about 300 psig to about 1500 psig and a temperature in the range from about 50° C. to about 150° C. to produce a mixture of reductively alkylated diamines in which the target diamine remains non-alkylated.

Preferred metals for the reductive alkylation are Raney nickel, finely divided iron, cobalt, platinum, palladium, ruthenium, osmium, rhenium and rhodium, any one of which is to be supported on pumice, asbestos, kieselguhr, alumina, silica gel or charcoal. The amount of catalyst used depends upon the process conditions and also upon the reactants, from about 0.01% to about 10% by wt of the diamines in the mixture being satisfactory.

The ketone used may be any branched or unbranched aliphatic ketones, preferably $C_3-C_8$, for example acetone, butanones, pentanones; and alicyclic ketones, preferably $C_5-C_8$, for example cyclopentanone, cyclohexanone, cyclooctanone.

When the process is practiced with an aliphatic ketone having from 3 to about 20 carbon atoms, preferably a lower $C_3-C_9$ ketone, or a $C_5-C_{20}$ cycloaliphatic ketone, and hydrogenation is effected over a Group VIII metal on a suitable catalyst support at a pressure in the range from about 500 psi to about 1000 psi and a temperature in the range from about 50° C. to about 200° C., no reaction product is isolated which is alkylated at the hindered $N^2$ atom of the target diamine.

Upon distillation of the reductively alkylated mixture of diamines, only the target diamine which will be cyclized to a fully hindered polysubstituted 1,4-diazacycloheptan-2-one is distilled overhead, while the reductively alkylated diamines remain. The reductive alkylation thus functions as a dynamic sieve which isolates the target diamine. The target diamine so obtained is then subjected to a ketoform reaction which results in an essentially pure fully hindered polysubstituted 1,4-diazacycloheptan-2-one.

The Ketoform Synthesis

The first mixture obtained as described hereinabove, or the dynamically sieved target diamine isolated as described, is reacted with a monoketone and the haloform, optionally with an inert organic solvent for the reactants, in the presence of aqueous alkali, optionally with a phase transfer catalyst. The reaction may be carried out at any temperature within a wide range from about ambient to about the reflux temperature of the solvent or reactants, provided such reflux temperature is lower than is deleterious to the polysubstituted 1,4-diazacycloheptan-2-one formed. The pressure at which the reaction is carried out is about atmospheric as there is generally no advantage to using higher pressure.

The most readily available preferred inert solvents are halohydrocarbons, preferably hydrochloromethylenes such as methylene chloride, sulfolane, dibutyl ether, dimethyl sulfone, diisopropyl ether, di-n-propyl ether, 1,4-dioxane, tetrahydrofuran, benzene and toluene, hexane, carbon tetrachloride and the like, which resist reduction under the conditions of reaction.

As an alternative, either chloroform or the ketone, each itself a reactant, may be used in large excess, so that the excess used functions as the solvent. The choice of whether to use the ketone or the chloroform as the solvent will depend in large part on the target diamine to be alkylated, and whether the ketoform reaction is to be conducted non-catalytically, that is, without a phase transfer catalyst.

The preferred aqueous alkali is an alkali metal hydroxide solution such as aqueous NaOH or KOH, preferably in the range from 20% to 70%. The amount used is not critical but it is preferred to use sufficient aqueous alkali to form a distinct visual phase in the presence of organic solvent. The amount of aqueous alkali is preferably at least 5% by weight of the reaction mass.

If an onium salt is used for a phase transfer catalyst, preferred onium salts are identified in the aforesaid Lai '497 and '512 patents. In general, it is sufficient to use less than 2 % by wt of the reaction mass, from 0.1 to 1% by wt being preferred.

If the ketoform reaction is to be non-catlaytic, at least a two-fold excess of ketone, over that stoichiometrically required, and preferably from about 4 to 16 times as much, is used.

The reaction mass from the ketoform reaction contains both the fully and partially hindered 1,4-diazacycloheptan-2-ones, or bis compounds thereof, all of which are typically either oils or solids.

If oils, the reductively alkylated materials are filtered to remove solid salt (say, NaCl) formed by the addition of alkali metal hydroxide (say sodium hydroxide, NaOH). An alternative is to dissolve the salt and any water-soluble components in water, then decant and save the organic layer for further work-up. The organic layer is distilled to remove unreacted ketone and other light (relatively low-boiling) compounds, which are discarded. Further distillation produces the product 1,4-diazacycloheptan-2-ones.

If solids, they are removed by filtration along with salt formed, the solids are then redissolved and re-precipitated from solvents in which the (1,4-diazacycloheptan-2-ones) are essentially completely soluble.

Preparation of the first mixture containing the target diamine

In a typical reaction, the first mixture of diamines is prepared from a 1-disubstituted-1,3-propanediprimaryamine for example, 2-methyl-2,4-pentane diamine by alkylating with $R^4X$ or $XR^5X$ where X is halogen, preferably Cl or Br, using conventional alkylation conditions, typically, ambient pressure and a temperature in the range from 50° C. to about 150° C. in a much lower molar amount than is required to alkylate only one primary amine group, preferably from about 5 mol % to 20 mol % of the starting diamine. The reaction is allowed to proceed for from 4 to 12 hr after which the excess starting diamine is distilled leaving the first mixture of alkylated diamines.

Preparation of the second mixture of polysubstituted 1,4-diazacycloheptan-2-ones The first mixture is then reacted with a ketone selected to provide particularly desirable physical properties in the product 1,4-diazacycloheptanones, for example lack of color and minimal toxicity, or to provide the desired steric hindrance in the product which is to be used for the stabilization of particular organic materials against degradation due to heat and light. The product is recovered as described hereinabove. The preparation of particular target diamines is illustrated in the following examples.

EXAMPLE 1

Alkylation of 2-methyl-2,4-pentanediamine ("DAMP") with octyl chloride

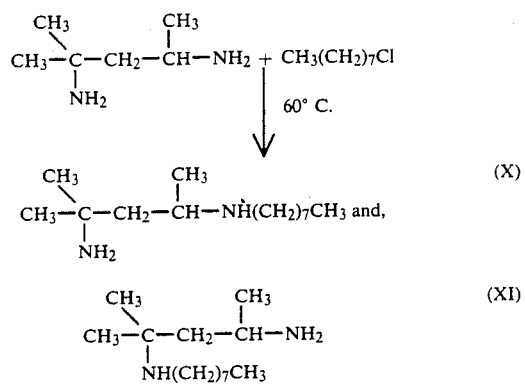

In a three-necked round-bottomed 100 ml jacketed flask fitted with a condenser, thermometer and magnetic stirrer are placed 46.4 g (0.4 mol) of "DAMP" (for diaminomethylpentane) and 5.95 g (0.04 mol) of octyl chloride. The flask was heated to 60° C. with stirring until the following morning (about 15 hr) when the excess DAMP was distilled. A GC (gas chromatographic) analysis of the residue shows that both (X) and (XI) are formed, but (X) is present in a major molar amount relative to (XI). The analysis was done in a Helwett Packard 5880 using a 6 ft glass column (2 mm i.d.) packed with 3% OV-17 on 100/120 Chromasorb WHP. The program had a starting temperature of 50° C., a program rate of 20° C. per min to 230° C. which was then held for 10 min. The structures (X) and (XI) written hereinabove are supported by both proton nuclear magnetic resonance (NMR), and field desorption (FD) mass spectroscopic data.

EXAMPLE 2

Preparation of polysubstituted 1,4-diazacycloheptan-2-ones (X) + (XI) + $CH_3-CO-CH_3$ + $CHCl_3$

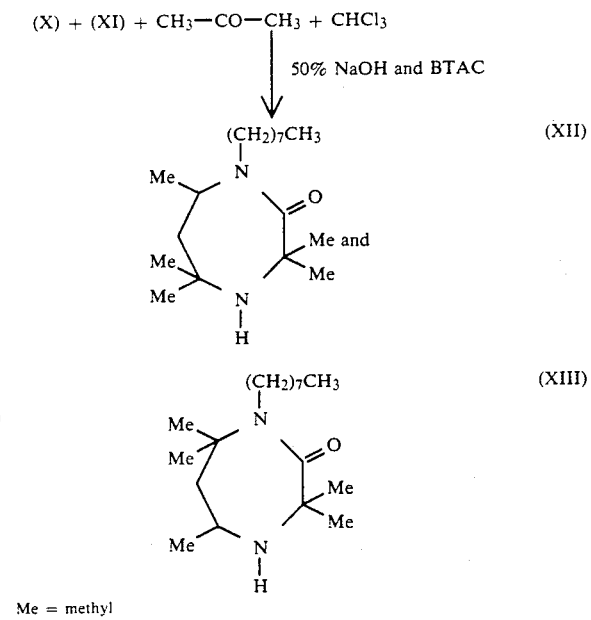

Me = methyl

11

In a three-necked round-bottomed 100 ml jacketed flask fitted with a condenser, thermometer and magnetic stirrer are placed 0.04 mol of the product, a major molar amount of which was (X), and 20 ml of chloroform, both warmed to 60° C. 0.2 g of benzyl triethylammonium chloride ("BTAC") is added and the mixture cooled to 10° C. before 2.32 g (0.04 mol) of acetone is added. Then 19.2 g (0.24 mol) ml of 50% NaOH are dripped in to control the exotherm and maintain a maximum temperature of about 18° C. With cooling, the temperature is lowered to, and maintained at about 10° C. for 3 hr with stirring. The reaction mixture is then worked up.

The solids are dissolved in water and the organic and the aqueous layer is separated. The aqueous layer is extracted with chloroform which is added to the organic layer which is then concentrated by evaporating the chloroform. The remaining concentrate contains the product along with a variety of unwanted by-products. The concentrate is distilled at 162°-170° C. at 2 mm Hg pressure to obtain the product which is a mixture of polysubstituted 1,4-diazacycloheptan-2-ones. The compounds (XII) and (XIII) are obtained in excellent yield and together are found to be more than 90% pure, (XII) being present in a major molar amount relative to (XIII).

EXAMPLE 3

Alkylation of 2-methyl-2,4-pentanediamine ("DAMP") with 2-chloroethanol

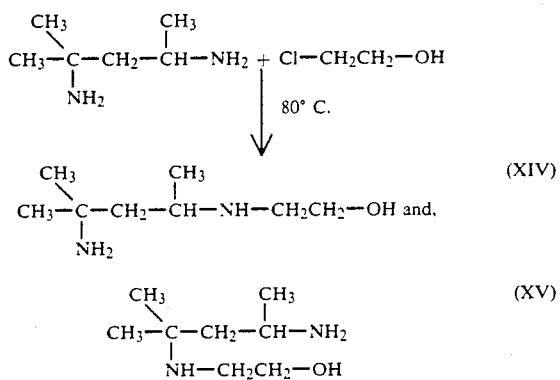

In a three-necked round-bottomed 250 ml jacketed flask fitted with Claisen adapter, condenser, etc. as before, are placed 116. g (1.0 mol) of DAMP and 8.05 g (0.1 mol) of 2-chloroethanol. The flask was heated to 80° C. and maintained at that temperature overnight, with stirring, after which the excess DAMP was distilled from the alkylated reaction mixture. A GC (gas chromatographic) analysis of the residue shows that a mixture of XIV and XV is formed, but that XIV is present in a major molar amount relative to XV. The structures XIV and XV written hereinabove are supported by both proton nuclear magnetic resonance (NMR), and field desorption (FD) mass spectroscopic data.

EXAMPLE 4

Preparation of polysubstituted 1,4-diazacycloheptan-2-ones

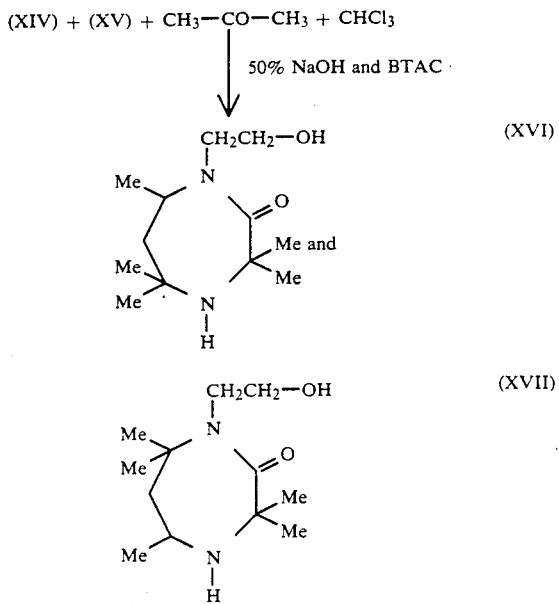

In a manner analogous to that described in example 2 hereinabove, the reactants, except NaOH are placed in a 300 ml jacketed flask, equipped as before, and cooled to about 10° C. Accordingly, about 0.1 mol of XIV and XV in which the former is present in about 60 mol % and the latter 40%, 17.91 g (0.15 mol) CHCl$_3$, 11.62 g (0.2 mol) acetone and 0.6 g BTAC are dissolved in 50 ml of CH$_2$Cl$_2$. Then 40 g (0.5 mol) of 50% NaOH solution is dripped in drop by drop. A soft white solid is formed. A maximum temperature of 18° C. is maintained while the reaction mass is stirred overnight. The reaction mass is worked up in the morning.

The liquid is decanted and the residue stirred with two 50 ml aliquots of CH$_2$Cl$_2$. The CH$_2$Cl$_2$ solutions are combined and concentrated by evaporating the solvent. The residue is then distilled to yield the product which is found to be a mixture of XVI and XVII, the former being present in a major molar amount, more than 80 mol % relative to about 20 mol % of XVII.

EXAMPLE 5

Alkylation of 2-methyl-2,4-pentanediamine ("DAMP") with 1,2-dichloroethane (EDC) to form a mixture of alkylated bis(diamine)s to be converted to a product of polysubstituted bis(1,4-diazacycloheptan-2-ones) as shown in Ex. 6

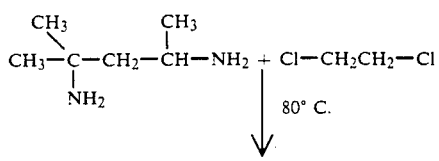

(XVIII)

$$\text{Me}-\underset{\underset{NH_2}{|}}{\overset{\overset{Me}{|}}{C}}-CH_2-\overset{Me}{\underset{|}{CH}}-NH-CH_2CH_2-NH-\overset{Me}{\underset{|}{CH}}-CH_2-\underset{\underset{NH_2}{|}}{\overset{\overset{Me}{/}}{C}}-\text{Me and,}$$

Me = methyl (XIX)

$$\left(H_2N-\overset{Me}{\underset{|}{CH}}-CH_2-\underset{\underset{NH---}{|}}{\overset{\overset{Me}{/}}{C}}-\text{Me}\right)-CH_2CH_2 \text{ and,}$$

(XX)

$$\text{Me}-\underset{\underset{-CH_2CH_2-HN}{|}}{\overset{\overset{Me}{\setminus}}{C}}-CH_2-\overset{Me}{\underset{|}{CH}}-NH-CH_2CH_2-NH-\overset{Me}{\underset{|}{CH}}-CH_2-\underset{\underset{NH-CH_2CH_2-}{|}}{\overset{\overset{Me}{/}}{C}}-\text{Me}$$

inter alia

In a three-necked round-bottomed 1 liter jacketed flask fitted with Claisen adapter, condenser, etc. as before, are placed 580 g (5.0 mol) of DAMP and heated to 80° C. while 49.5 g (0.5 mol) of EDC is dripped into the flask drop by drop over 2 hr. The flask was maintained at that temperature for about 4.5 hr more, with stirring, after which the alkylated reaction mass is worked up.

Add 96 g (1.2 mols) of 50% NaOH stir overnight and let cool. Then filter and distill the excess DAMP. The residue is further distilled to collect 66 g cf a colorless oil boiling at 136°-142° C. at 2.3 mm Hg pressure. A residue of 8.4 g of heavies is left in the pot.

A GC (gas chromatographic) analysis of the residue shows that a mixture of XVIII and XIX and XX, and others, is formed, but that XVIII is present in a major molar amount relative to the others combined. The structures XVIII and XIX written hereinabove are supported by both proton nuclear magnetic resonance (NMR), and field desorption (FD) mass spectroscopic data.

EXAMPLE 6

Preparation of polysubstituted
bis-(1,4-diazacycloheptan-2-ones)

(XVIII) + (XIX) + (XX) + CH₃—CO—CH₃ + CHCl₃

|
| 50% NaOH and BTAC
↓

(XXI')

$$\text{structure with } CH_2CH_2 \text{ bridge connecting two diazacycloheptan-2-one rings with Me substituents}$$

and other polysubstituted
bis-(1,4-diazacycloheptan-2-ones) not shown

In a manner analogous to that described in example 2 hereinabove, the reactants, except NaOH are placed in a 500 ml jacketed flask, equipped as before, and cooled to about 10° C. Accordingly, about 26 g (0.1 mol) of XVIII, XIX and XX in which the XVIII is present in about 60 mol % and the others together about 40%, 29.85 g (0.25 mol) CHCl₃, 14.53 g (0.25 mol) acetone and 0.5 g BTAC are dissolved in 90 ml of CH₂Cl₂. Then 40 g (1 mol) of solid NaOH is added in portions maintaining the temperature at 10° C. or lower to avoid a high exotherm. The reaction mass turns white. It is stirred overnight at 10° C. and worked up in the morning.

The reaction mass is filtered and the solids rinsed with methylene chloride. The filtrate is washed with 40 ml of saturated NaCl and the CH₂Cl₂ distilled off. The residue is stirred with hexane and cooled to precipitate 12.5 g of white solid. The filtrate is concentrated, stirred in hexane and an additional 2.0 g of white solid are recovered. The white solid is more than 80% XXI'.

It will now be evident that a wide variety of substituents may be made in the 3, 5 and 7 positions of the polysubstituted 1,4-diazacycloheptan-2-one compounds formed, and because of the idiosyncracy of the reaction, particularly with a substituent in the 7 position of the ring, the desired polysubstituted 1,4-diazacycloheptan-2-one with the fully hindered N⁴ atom will be formed in a major molar amount relative to any other polysubstituted 1,4-diazacycloheptan-2-one. The effect of making various substituents can be judged by simple trial and error until the optimum properties are obtained for the purpose at hand.

Of course, such optimum properties of a polysubstituted 1,4-diazacycloheptan-2-one can best be judged only with an essentially pure mass of the desired polysubstituted 1,4-diazacycloheptan-2-ones which are free from unwanted byproducts, particularly those acyclic alkylated diamines having both secondary amino groups, and oligomers formed from them. We know of no process, other than the one we have disclosed hereinabove, which will provide the essentially pure mass of polysubstituted 1,4-diazacycloheptan-2-one without making a separation of individual alkylated diamines.

I claim:

1. A process for making 1,4-diazacycloheptan-2-ones, and bis-compounds thereof, from a mixture of 1-disubstituted-b 1,3-propanediamines all present in a first mixture of alkylated diamines represented by the following structural formulae, and bis-compounds thereof:

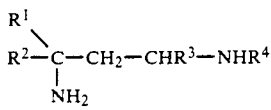

(I)
$$R^2-\underset{\underset{NH_2}{|}}{\overset{\overset{R^1}{\diagdown}}{C}}-CH_2-CHR^3-NHR^4$$

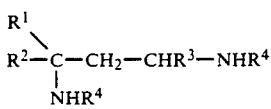

(VI)
$$R^2-\underset{\underset{NHR^4}{|}}{\overset{\overset{R^1}{\diagdown}}{C}}-CH_2-CHR^3-NHR^4$$

and,

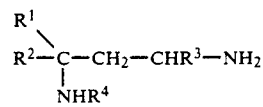

(VII)
$$R^2-\underset{\underset{NHR^4}{|}}{\overset{\overset{R^1}{\diagdown}}{C}}-CH_2-CHR^3-NH_2$$

wherein,
$R^1$, $R^2$, and $R^3$ independently represent $C_1$-$C_{24}$ alkyl; $R^3$, but only one of $R^1$ and $R^2$, represent $C_7$-$C_{20}$ aralkyl;

$R^4$ represents $C_1$-$C_{20}$ alkyl, $C_5$-$C_{24}$ cycloalkyl or alkyl-substituted cycloalkyl the cycloalkyl ring being $C_5$-$C_8$; $C_7$-$C_{20}$ aralkyl; and $R^1R^2C=CR^1CH$—; and, $R^1$ and $R^2$ together when cyclized represent $C_5$-$C_7$ cycloalkyl;

wherein target diamine (I) has a molecular weight too close to that of (VI) and (VII) to be separable therefrom by conventional separation processes, comprising, (a) reacting said first mixture with a ketone having the structure

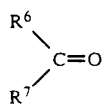

$$\underset{R^7}{\overset{R^6}{\diagdown}}C=O$$

and a haloform $CHX_3$ wherein X is Cl, or Br; wherein, $R^6$ and $R^7$ independently each represent $C_1$-$C_{18}$ alkyl, and when together cyclized represent $C_5$-$C_8$ cycloalkyl; in the presence of a base, an organic solvent and optionally a phase transfer catalyst to form 1,4-diazacycloheptan-2-ones having the structures

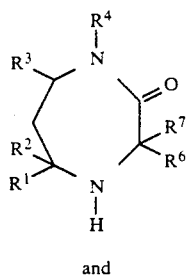

(IV)

and

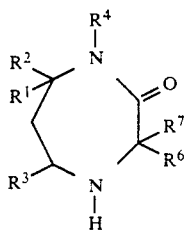

(V)

in a second mixture of cyclic and acyclic diamines; and, (b) separating a product from all other components of said second reaction mixture, said product consisting essentially of a major molar proportion of (IV) relative to (V); and, (IV) and (V) together constitute at least 90% by weight of said product.

2. The process of claim 1 wherein $R^1$ and $R^2$, when together cyclized are $C_5$-$C_6$ cycloalkyl, or are independently each selected from $C_1$-$C_6$ alkyl; $R^3$ is $C_1$-$C_6$ alkyl; and said said organic solvent is a halohydrocarbon.

3. The process of claim 1 wherein $R^1$ and $R^2$, when together cyclized are $C_5$-$C_6$ cycloalkyl, or are independently each selected from $C_1$-$C_6$ alkyl; $R^3$ is $C_1$-$C_6$ alkyl; and said organic solvent is a reactant selected from said ketone and said haloform.

4. The process of claim 1 wherein said ketone is selected from the group consisting of $C_3$-$C_{20}$ branched or unbranched aliphatic ketones, and $C_5$-$C_8$ alicyclic ketones present in about a stoichiometric amount, and said haloform is chloroform.

5. The process of claim 1 wherein $R^1$ and $R^2$ are independently each selected from $C_1$-$C_6$ alkyl; said ketone is selected from the group consisting of $C_3$-$C_{20}$ branched or unbranched aliphatic ketones present in at least a two-fold molar excess, said haloform is chloroform, and said phase transfer catalyst is absent.

6. A process for making a polysubstituted 1,4-diazacycloheptan-2-one with a fully hindered unsubstituted $N^4$ atom, and bis-compounds thereof, from a mixture of 1-disubstituted-1,3-propanediamines all present in a first mixture of alkylated diamines represented by the following structural formulae, and bis-compounds thereof:

(I)
$$R^2-\underset{\underset{NH_2}{|}}{\overset{\overset{R^1}{\diagdown}}{C}}-CH_2-CHR^3-NHR^4$$

(VI)
$$R^2-\underset{\underset{NHR^4}{|}}{\overset{\overset{R^1}{\diagdown}}{C}}-CH_2-CHR^3-NHR^4$$

and, (VII)
$$R^2-\underset{\underset{NHR^4}{|}}{\overset{\overset{R^1}{\diagdown}}{C}}-CH_2-CHR^3-NH_2$$

wherein,
$R^1$, $R^2$, and $R^3$ independently represent $C_1$-$C_{24}$ alkyl; $R^3$, but only one of $R^1$ and $R^2$, represent $C_7$-$C_{20}$ aralkyl;

$R^4$ represents $C_1$-$C_{20}$ alkyl, $C_5$-$C_{24}$ cycloalkyl or alkyl-substituted cycloalkyl the cycloalkyl ring being $C_5C_8$; $C_7$-$C_{20}$ aralkyl; and $R^1R^2C=CR^1CH_2$—; and, $R^1$ and $R^2$ together when cyclized represent $C_5$-$C_7$ cycloalkyl;

wherein target diamine (I) has a molecular weight so close to that of (VI) and (VII) as to be inseparable (I) from the others by conventional separation processes, comprising, (a) contacting said first mixture with hydrogen and a ketone in the presence of a catalytically effective amount of a Group VIII metal on a catalyst support, at a pressure in the range from about 500–1000 psi and a temperature in the range from about 50° C. to about 200° C. for a period of time sufficient, preferentially, to reductively alkylate said $N^1$-containing amino group essentially without alkylating the $N^2$-containing primary amino group, so as to form a third mixture of said target diamine in reductively alkylated diamines, (b) separating said target diamine from other reductively alkylated diamines and compounds in said third mixture to obtain an essentially pure target diamine, and, (c) reacting said target diamine with a ketone having the structure

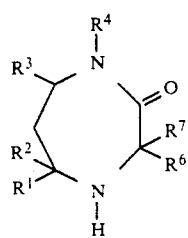

and a haloform $CHX_3$ wherein X is Cl, or Br; wherein, $R^6$ and $R^7$ represent $C_1$–$C_{18}$ alkyl, and when together cyclized represent $C_5$–$C_8$ cycloalkyl; in the presence of a base and optionally, a phase transfer catalyst and solvent for the reactants, to form a 1,4-diazacycloheptan-2-one having the structure

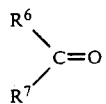

in a second mixture of cyclic and acyclic diamines; and, (d) recovering the esentially pure 1,4-diazacycloheptan-2-one (IV) from said second reaction mixture.

7. The process of claim 6 wherein said Group VIII metal is selected from the group consisting of nickel, platinum, rhenium, rhodium, ruthenium and palladium, and hydrogenation is carried out in the presence of a solvent for the reactants, which solvent is inert under hydrogenation conditions.

8. The process of claim 7 wherein $R^1$ and $R^2$, when together cyclized are $C_5$–$C_6$ cycloalkyl, or are independently each selected from $C_1$–$C_6$ alkyl, $R^3$ is $C_1$–$C_6$ alkyl, and said organic solvent is a halohydrocarbon.

9. The process of claim 7 wherein $R^1$ and $R^2$, when together cyclized are $C_5$–$C_6$ cycloalkyl, or are independently each selected from $C_1$–$C_6$ alkyl, $R^3$ is $C_1$–$C_6$ alkyl, and said organic solvent is a reactant selected from said ketone and said haloform.

10. The process of claim 6 wherein said ketone is selected from the group consisting of $C_3$–$C_{20}$ branched or unbranched aliphatic ketones, and $C_5$–$C_8$ alicyclic ketones present in about a stoichiometric amount, and said haloform is chloroform.

11. The process of claim 10 wherein $R^1$ and $R^2$ are independently each selected from $C_1$–$C_6$ alkyl; said ketone is selected from the group consisting of $C_3$–$C_{20}$ branched or unbranched aliphatic ketones present in at least a two-fold molar excess, said haloform is chloroform, and said phase transfer catalyst is absent.

12. A process for making polysubstitued 1,4-diazacycloheptan-2-ones, comprising, (a) reacting a molar excess of a 1-disubstituted-1,3-propane diamine (starting diamine) with an alkylating agent $R^4X$ in a molar ratio of at least 3:1, to form a mixture of alkylated 1-disubstituted-1,3-propanediamines represented by the following structural formulae:

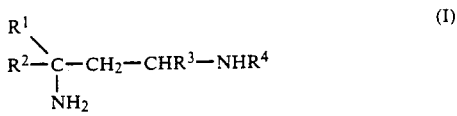

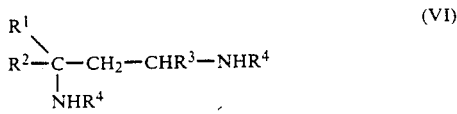

and,

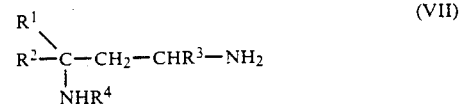

wherein, $R^1$, $R^2$, and $R^3$ independently represent $C_1$–$C_{24}$ alkyl;

$R^3$, but only one of $R^1$ and $R^2$, represent $C_7$–$C_{20}$ aralkyl;

$R^4$ represents $C_1$–$C_{20}$ alkyl, $C_5$–$C_{24}$ cycloalkyl or alkyl-substituted cycloalkyl the cycloalkyl ring being $C_5C_8$; $C_7$–$C_{20}$ aralkyl; and $R^1R^2C\!=\!CR^1CH$ —; and, $R^1$ and $R^2$ together when cyclized represent $C_5$–$C_7$ cycloalkyl;

wherein target diamine (I) has a molecular weight too close to that of (VI) and (VII) to be separable therefrom by conventional separation processes;

(b) removing the excess of unreacted starting diamine to provide a first mixture of alkylated diamines;

(c) reacting said first mixture with a ketone having the structure

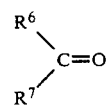

and a haloform $CHX_3$ wherein X is Cl, or Br; wherein, $R^6$ and $R^7$ independently each represent $C_1$—$C_{18}$ alkyl, and when together cyclized represent $C_5$–$C_8$ cycloalkyl; in the presence of a base, an organic solvent and optionally a phase transfer catalyst to form 1,4-diazacycloheptan-2-ones having the structures

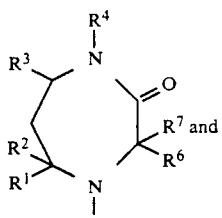

(IV)

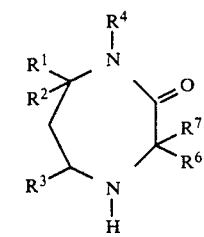

(V)

present in a second reaction mixture of cyclic and acyclic diamines;

(c) separating a product from all other components of said second reaction mixture, said product consisting essentially of a major molar proportion of (IV) relative to (V).

13. The process of claim 12 wherein $R^1$ and $R^2$, when together cyclized are $C_5$–$C_6$ cycloalkyl, or are independently each selected from $C_1$–$C_6$ alkyl; $R^3$ is $C_1$–$C_6$ alkyl; and said said organic solvent is a halohydrocarbon.

14. The process of claim 12 wherein $R^1$ and $R^2$, when together cyclized are $C_5$–$C_6$ cycloalkyl, or are independently each selected from $C_1$–$C_6$ alkyl; $R^3$ is $C_1$–$C_6$ alkyl; and said organic solvent is a reactant selected from said ketone and said haloform.

15. The process of claim 12 wherein said ketone is selected from the group consisting of $C_3$–$C_{20}$ branched or unbranched aliphatic ketones, and $C_5$–$C_8$ alicyclic ketones present in about a stoichiometric amount, and said haloform is chloroform.

16. The process of claim 12 wherein $R^1$ and $R^2$ are independently each selected from $C_1$–$C_6$ alkyl; said ketone is selected from the group consisting of $C_3$–$C_{20}$ branched or unbranched aliphatic ketones present in at least a two-fold molar excess, said haloform is chloroform, and said phase transfer catalyst is absent.

17. A process for making polysubstitued 1,4-diazacycloheptan-2-ones, comprising, (a) reacting a molar excess of a 1-disubstituted-1,3-propane diamine with an alkylating agent $R^4X$ in a molar ratio of at least 3:1, to form a mixture of alkylated 1-disubstituted-1,3-propanediamines represented by the following structural formulae:

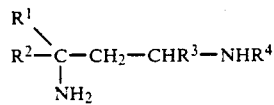

(I)

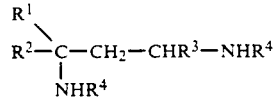

(VI)

and,

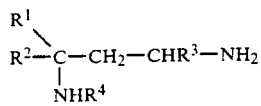

(VII)

wherein, $R^1$, $R^2$, and $R^3$ independently represent $C_1$–$C_{24}$ alkyl;

$R^3$, but only one of $R^1$ and $R^2$, represent $C_7$–$C_{20}$ aralkyl;

$R^4$ represents $C_1$–$C_{20}$ alkyl, $C_5$–$C_{24}$ cycloalkyl or alkyl substituted cycloalkyl the cycloalkyl ring being $C_5C_8$; $C_7$–$C_{20}$ aralkyl; and $R^1R^2C=CR^1CH_2$—; and, $R^1$ and $R^2$ together when cyclized' represent $C_5$–$C_7$ cycloalkyl;

wherein target diamine (I) has a molecular weight too close to that of (VI) and (VII) to be separable therefrom by conventional separation processes;

(b) removing excess starting diamine to provide a mixture of said alkylated diamines in a first mixture;

(c) contacting said first mixture with hydrogen and a ketone in the presence of a catalytically effective amount of a Group VIII metal on a catalyst support, at a pressure in the range from about 500–1000 psi and a temperature in the range from about 50° C. to about 200° C. for a period of time sufficient to preferentially reductively alkylate said $N^1$-containing amino group essentially without alkylating the $N^2$-containing primary amino group, so as to form a third mixture of said target diamine in reductively alkylated diamines, (d) separating said target diamine from other reductively alkylated diamines and compounds in said third mixture to obtain an essentially pure target diamine, (e) reacting said target diamine with a ketone having the structure

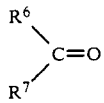

and a haloform $CHX_3$ wherein X is Cl, or Br; wherein, $R^6$ and $R^7$ independently each represent $C_1$–$C_{18}$ alkyl, and when together cyclized represent $C_5$–$C_8$ cycloalkyl; in the presence of a base and optionally, a phase transfer catalyst and solvent for the reactants, to form a 1,4-diazacycloheptan-2-one having the structure

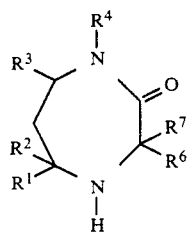

(IV)

in a second mixture of cyclic and acyclic diamines; and, (f) recovering the essentially pure 1,4-diazacycloheptan-2-one (IV) from said second reaction mixture.

18. The process of claim 17 wherein said Group VIII metal is selected from the group consisting of nickel, platinum, rhenium, rhodium, ruthenium and palladium, and hydrogenation is carried out in the presence of a solvent for the reactants, which solvent is inert under hydrogenation conditions.

19. The process of claim 17 wherein $R^1$ and $R^2$, when together cyclized are $C_5-C_6$ cycloalkyl, or are independently each selected from $C_1-C_6$ alkyl, $R^3$ is $C_1-C_6$ alkyl, and said organic solvent is a halohydrocarbon.

20. The process of claim 17 wherein $R^1$ and $R^2$, when together cyclized are $C_5-C_6$ cycloalkyl, or are independently each selected from $C_1-C_6$ alkyl, $R^3$ is $C_1-C_6$ alkyl, and said organic solvent is a reactant selected from said ketone and said haloform.

21. The process of claim 17 wherein said ketone is selected from the group consisting of $C_3-C_{20}$ branched or unbranched aliphatic ketones, and $C_5-C_8$ alicyclic ketones present in about a stoichiometric amount, and said haloform is chloroform.

22. The process of claim 19 wherein said halohydrocarbon is a hydrochloromethylene.

23. The process of claim 17 wherein $R^1$ and $R^2$ are independently each selected from $C_1-C_6$ alkyl; said ketone is selected from the group consisting of $C_3-C_{20}$ branched or unbranched aliphatic ketones present in at least a twofold molar excess, said haloform is chloroform, and said phase transfer catalyst is absent.

24. A process for making bis-compounds of 1,4-diazacycloheptan-2-ones, comprising,
  (a) reacting an excess of 1-disubstituted-1,3-propane diamine with an alkylating agent $XR^5X$ in a molar ratio of at least 3:1, to form a mixture of bis(alkylated 1-disubstituted-1,3-propanediamines) represented by the following structural formulae:

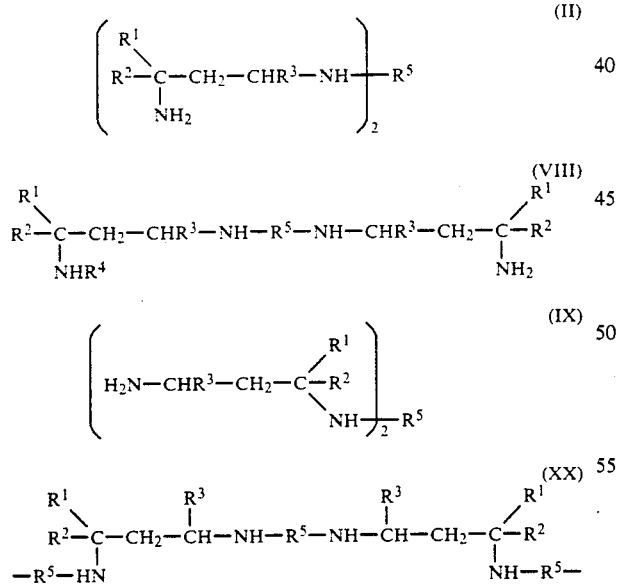

and oligomers thereof containing from 3 to about 6 diamine repeating units,
  $R^1$, $R^2$, and $R^3$ independently represent $C_1-C_{24}$ alkyl;
  $R^3$, but only one of $R^1$ and $R^2$, represent $C_7-C_{20}$ aralkyl; and,
  $R^5$ represents $C_2-C_{24}$ alkylene, $R^5$-substituted $C_9-C_{23}$ cycloalkyl the cycloalkyl ring being $C_5-C_8$, $R^8-Ph-R^8$ wherein Ph represents phenyl and $R^8$ represents $C_2-C_{12}$ alkylene;
  wherein target diamine (II) has a molecular weight too close to that of (IX), and other bis(alkylated diamines) to be separable therefrom by conventional separation processes;
  (b) removing excess starting diamine to provide a mixture of alkylated bis-diamines and said oligomers in a first mixture;
  (c) reacting said first mixture with a ketone having the structure

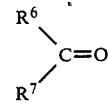

and a haloform $CHX_3$ wherein X is Cl, or Br; wherein, $R^6$ and $R^7$ independently each represent $C_1-C_{18}$ alkyl, and when together cyclized represent $C_5-C_8$ cycloalkyl; in the presence of a base, an organic solvent and optionally a phase transfer catalyst to form a bis(1,4-diazacycloheptan-2-one) having the structure

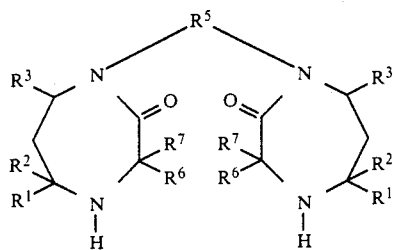

in a second reaction mixture of cyclic and acyclic diamines; and,
  (d) separating a product from all other components of said second reaction mixture, said product consisting essentially of a major molar proportion of (XXI) in a mixture of bis(1,4-diazacyclo-heptan-2-one)s.

25. The process of claim 24 wherein $R^1$ and $R^2$, when together cyclized are $C_5-C_6$ cycloalkyl, or are independently each selected from $C_1-C_6$ alkyl; $R^3$ is $C_1-C_6$ alkyl; and said said organic solvent is a halohydrocarbon.

26. The process of claim 24 wherein $R^1$ and $R^2$, when together cyclized are $C_5-C_6$ cycloalkyl, or are independently each selected from $C_1-C_6$ alkyl; $R^3$ is $C_1-C_6$ alkyl; and said organic solvent is a reactant selected from said ketone and said haloform.

27. The process of claim 24 wherein said ketone is selected from the group consisting of $C_3-C_{20}$ branched or unbranched aliphatic ketones, and $C_5-C_8$ alicyclic ketones present in about a stoichiometric amount, and said haloform is chloroform.

28. The process of claim 24 wherein $R^1$ and $R^2$ are independently each selected from $C_1-C_6$ alkyl; said ketone is selected from the group consisting of $C_3-C_{20}$ branched or unbranched aliphatic ketones present in at least a two-fold molar excess, said haloform is chloroform, and said phase transfer catalyst is absent.

29. A process for making bis-compounds of 1,4-diazacycloheptan-2-ones, comprising,
  (a) reacting an excess of 1-disubstituted-1,3-propane diamine with an alkylating agent $XR^5X$ in a molar ratio of at least 3:1, to form a mixture of bis(alkylated 1-disubstituted-1,3-propanediamines) represented by the following structural formulae:

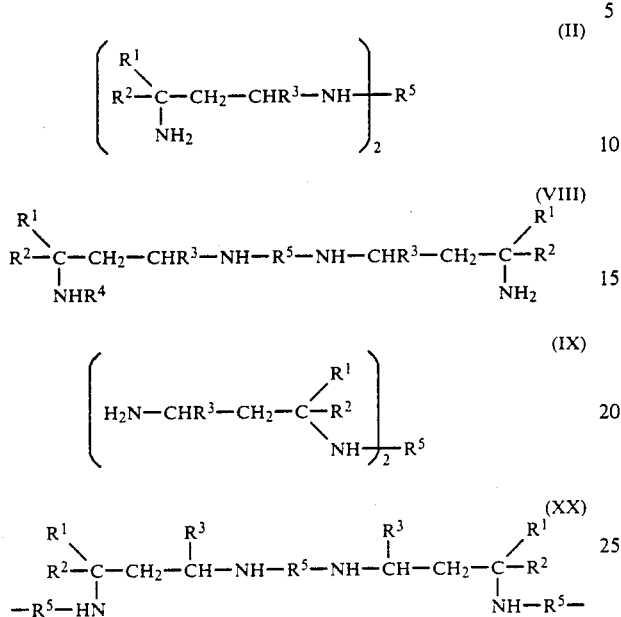

and oligomers thereof containing from 3 to about 6 diamine repeating units, wherein, $R^1$, $R^2$, and $R^3$ independently represent $C_1$–$C_{24}$ alkyl;

$R^3$, but only one of $R^1$ and $R^2$, represent $C_7$–$C_{20}$ aralkyl; and, $R^5$ represents $C_2$–$C_{24}$ alkylene, $R^5$-substituted $C_9$–$C_{23}$ cycloalkyl the cycloalkyl ring being $C_5$–$C_8$, and, $R^8$—Ph—$R^8$ wherein Ph represents phenyl and $R^8$ represents $C_2$–$C_{12}$ alkylene;

wherein target diamine (II) has a molecular weight too close to that of (IX), and other bis(alkylated diamines) to be separable therefrom by conventional separation processes;

(b) contacting said first mixture with hydrogen and a ketone in the presence of a catalytically effective amount of a Group VIII metal on a catalyst support, at a pressure in the range from about 500–1000 psi and a temperature in the range from about 50° C. to about 200° C. for a period of time sufficient to preferentially reductively alkylate said $N^1$-containing amino group essentially without alkylating the $N^2$-containing primary amino group, so as to form a third mixture of said target diamine in reductively alkylated diamines, (c) separating said target diamine from other reductively alkylated diamines and compounds in said third mixture to obtain an essentially pure target diamine, (d) reacting said first mixture with a ketone having the structure

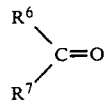

and a haloform $CHX_3$ wherein X is Cl, or Br; wherein, $R^6$ and $R^7$ independently each represent $C_1$–$C_8$ alkyl, and when together cyclized represent $C_5$–$C_8$ cycloalkyl; in the presence of a base, an organic solvent and optionally a phase transfer catalyst to form a bis(1,4-diazacycloheptan-2-one) having the structure

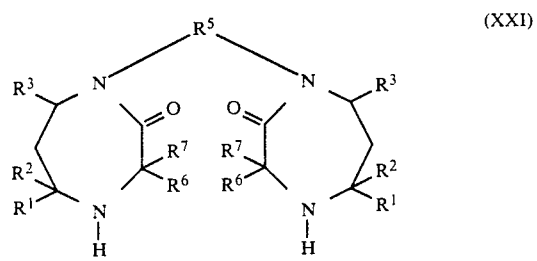

in a second reaction mixture of cyclic and acyclic bis(diamines) and oligomers containing from 2 to 6 diamine repeating units; and, (d) recovering the essentially pure bis(1,4-diazacycloheptan-2-one) (XXI) from said second reaction mixture.

30. The process of claim 29 wherein said Group VIII metal is selected from the group consisting of nickel, platinum, rhenium, rhodium, ruthenium and palladium, and hydrogenation is carried out in the presence of a solvent for the reactants, which solvent is inert under hydrogenation conditions.

31. The process of claim 29 wherein $R^1$ and $R^2$, when together cyclized are $C_5$–$C_6$ cycloalkyl, or are independently each selected from $C_1$–$C_6$ alkyl, $R^3$ is $C_1$–$C_6$ alkyl, and said organic solvent is a halohydrocarbon.

32. The process of claim 29 wherein $R^1$ and $R^2$, when together cyclized are $C_5$–$C_6$ cycloalkyl, or are independently each selected from $C_1$–$C_6$ alkyl, $R^3$ is $C_1$–$C_6$ alkyl, and said organic solvent is a reactant selected from said ketone and said haloform.

33. The process of claim 32 wherein said ketone is selected from the group consisting of $C_3$–$C_{20}$ branched or unbranched aliphatic ketones, and $C_5$–$C_8$ alicyclic ketones present in about a stoichiometric amount, and said haloform is chloroform.

34. The process of claim 29 wherein $R^1$ and $R^2$ are independently each selected from $C_1$–$C_6$ alkyl; said ketone is selected from the group consisting of $C_3$–$C_{20}$ branched or unbranched aliphatic ketones present in at least a two-fold molar excess, said haloform is chloroform, and said phase transfer catalyst is absent.

* * * * *